United States Patent
Hasegawa

(10) Patent No.: US 10,314,767 B2
(45) Date of Patent: Jun. 11, 2019

(54) DISPENSING INSPECTION DEVICE, DISPENSING INSPECTION METHOD, AND RECORDING MEDIUM

(71) Applicant: FUJIFILM Corporation, Tokyo (JP)

(72) Inventor: Kazuhide Hasegawa, Ashigara-kami-gun (JP)

(73) Assignee: FUJIFILM Corporation, Minato-Ku, Tokyo (JP)

( * ) Notice: Subject to any disclaimer, the term of this patent is extended or adjusted under 35 U.S.C. 154(b) by 21 days.

(21) Appl. No.: 15/805,515

(22) Filed: Nov. 7, 2017

(65) Prior Publication Data

US 2018/0055736 A1    Mar. 1, 2018

Related U.S. Application Data

(63) Continuation of application No. PCT/JP2016/065181, filed on May 23, 2016.

(30) Foreign Application Priority Data

May 29, 2015   (JP) ................ 2015-109826

(51) Int. Cl.
*G06K 9/00*  (2006.01)
*A61J 7/02*  (2006.01)
(Continued)

(52) U.S. Cl.
CPC ........... *A61J 7/02* (2013.01); *A61J 7/0076* (2013.01); *G06K 7/10* (2013.01); *G06K 7/1413* (2013.01);
(Continued)

(58) Field of Classification Search
None
See application file for complete search history.

(56) References Cited

U.S. PATENT DOCUMENTS

2008/0000979 A1* 1/2008 Poisner ............ G06K 19/06046
                                                                235/462.01
2009/0012818 A1* 1/2009 Rodgers ................ G01G 17/00
                                                                705/3
(Continued)

FOREIGN PATENT DOCUMENTS

JP    2004-167158 A    6/2004
JP    2008119443 A     5/2008
(Continued)

OTHER PUBLICATIONS

International Search Report dated Jul. 12, 2016, issued by the International Bureau in counterpart Application No. PCT/JP2016/065181.
(Continued)

*Primary Examiner* — Sean M Conner
(74) *Attorney, Agent, or Firm* — Sughrue Mion, PLLC

(57) ABSTRACT

There are provided a dispensing inspection device, a dispensing inspection method, a program, and a recording medium capable of inspecting whether dispensing is appropriately performed with high reliability. By obtaining a first image captured by imaging a rear surface of a medicine sheet and a second image obtained by imaging a lateral side thereof, and a third image obtained by irradiating a front surface of a fractional medicine with light from an inclined lower side, detecting a medicine name using OCR and/or code recognition from the first image, detecting the number of medicine sheets from the second image, detecting the number of fractional medicines from the third image, detecting a total number of medicines from the number of the medicine sheets and the number of the fractional medicines, and determining whether a medicine name and the number of medicines in prescription information and the detected
(Continued)

medicine name and the detected total number of medicines match each other.

20 Claims, 8 Drawing Sheets

(51) Int. Cl.
| | |
|---|---|
| G06K 7/10 | (2006.01) |
| G06Q 50/24 | (2012.01) |
| G06T 7/13 | (2017.01) |
| A61J 7/00 | (2006.01) |
| G06K 7/14 | (2006.01) |
| G06K 9/20 | (2006.01) |
| G06K 9/34 | (2006.01) |
| G06K 9/62 | (2006.01) |
| G06T 7/00 | (2017.01) |
| A61J 1/03 | (2006.01) |
| G01N 21/95 | (2006.01) |

(52) U.S. Cl.
CPC ............ *G06K 9/209* (2013.01); *G06K 9/344* (2013.01); *G06K 9/6201* (2013.01); *G06Q 50/24* (2013.01); *G06T 7/0014* (2013.01); *G06T 7/13* (2017.01); *A61J 1/035* (2013.01); *A61J 2205/10* (2013.01); *G01N 21/9508* (2013.01); *G06K 2209/01* (2013.01); *G06K 2209/19* (2013.01); *G06K 2209/21* (2013.01); *G06T 2207/30232* (2013.01); *G06T 2207/30242* (2013.01)

(56) References Cited

U.S. PATENT DOCUMENTS

| | | | |
|---|---|---|---|
| 2010/0042395 A1* | 2/2010 | Rothschild | G06F 19/326 703/12 |
| 2012/0330684 A1 | 12/2012 | Jacobs et al. | |
| 2015/0170373 A1 | 6/2015 | Yonaha et al. | |
| 2015/0178674 A1 | 6/2015 | Yonaha et al. | |
| 2016/0104277 A1 | 4/2016 | Takamori | |

FOREIGN PATENT DOCUMENTS

| | | |
|---|---|---|
| JP | 2010086257 A | 4/2010 |
| JP | 2013-529095 A | 7/2013 |
| JP | 2013-214170 A | 10/2013 |
| JP | 2014-064836 A | 4/2014 |
| JP | 2014-221134 A | 11/2014 |
| JP | 2015057114 A | 3/2015 |
| JP | 2015-080512 A | 4/2015 |
| WO | 2014/050486 A1 | 4/2014 |
| WO | 2014203748 A1 | 12/2014 |

OTHER PUBLICATIONS

International Preliminary Report on Patentability issued from the International Bureau in counterpart International Application No. PCT/JP2016/065181, dated Dec. 5, 2017.
Translation of Written Opinion dated Jul. 12, 2016, issued by the International Bureau in counterpart Application No. PCT/JP2016/065181.
Communication dated May 2, 2018, from the European Patent Office in counterpart European Application No. 16803115.1.
Communication dated Dec. 18, 2018, from the Japanese Patent Office in counterpart application No. 2017-521823.

* cited by examiner

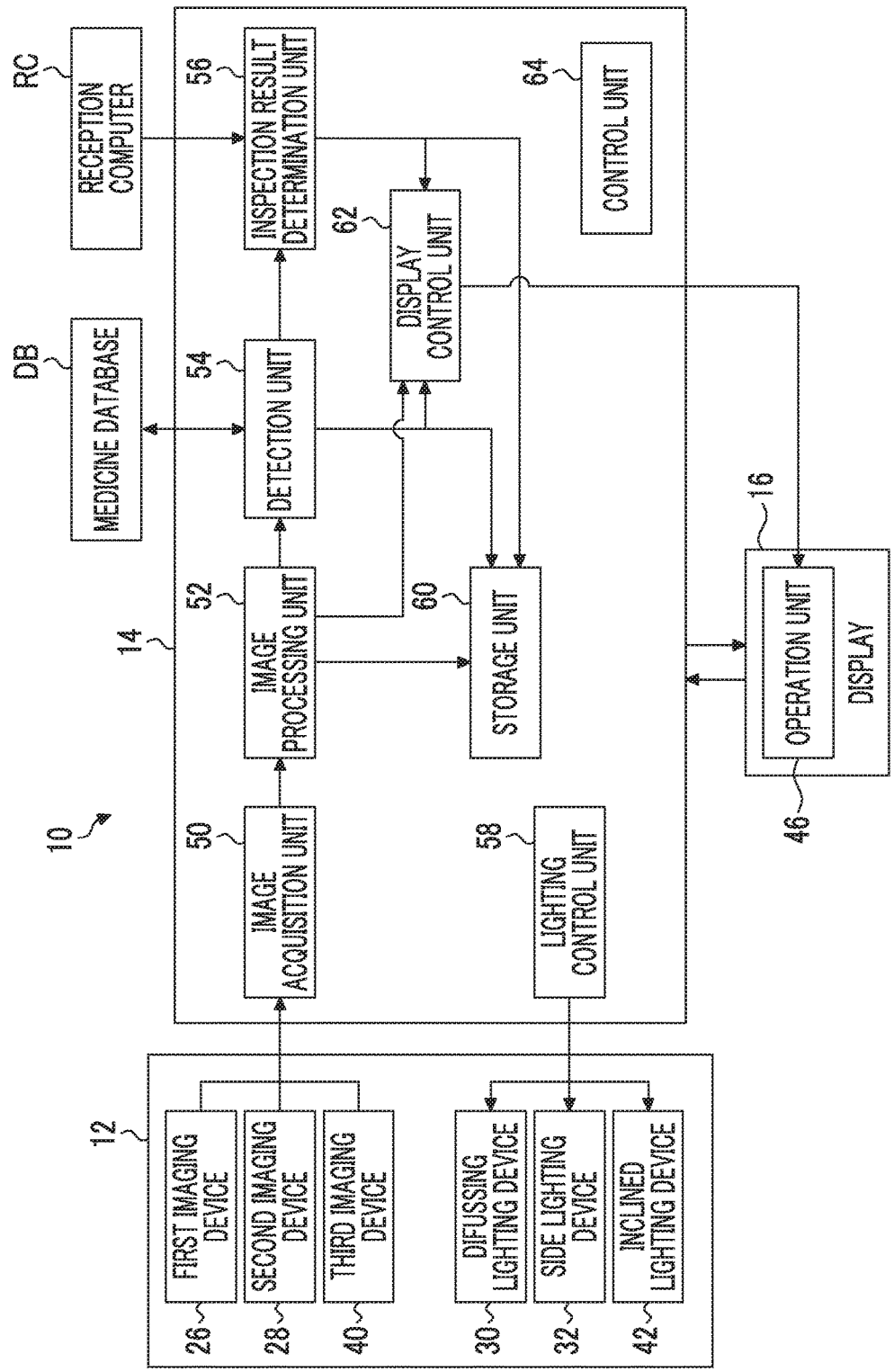

FIG. 8A          FIG. 8B          FIG. 8C

```
PRESCRIPTION No. 12345
MEDICINE: GLUCO ○○ 100
THE NUMBER: ??

INSPECTION RESULT
○ PASS
```

```
PRESCRIPTION No. 12345
MEDICINE: GLUCO ○○ 100
THE NUMBER: ??

INSPECTION RESULT
× EXCESS
```

```
PRESCRIPTION No. 12345
MEDICINE: GLUCO ○○ 100
THE NUMBER: ??

INSPECTION RESULT
× SHORTAGE
   (ADDITIONAL INPUT?)
```

DISPENSING INSPECTION DEVICE, DISPENSING INSPECTION METHOD, AND RECORDING MEDIUM

CROSS-REFERENCE TO RELATED APPLICATIONS

This application is a Continuation of PCT International Application No. PCT/JP2016/065181 filed on May 23, 2016, which claims priority under 35 U.S.C. § 119(a) to Japanese Patent Application No. 2015-109826 filed on May 29, 2015. The above application is hereby expressly incorporated by reference, in its entirety, into the present application.

BACKGROUND OF THE INVENTION

1. Field of the Invention

The present invention relates to a dispensing inspection technique, and particularly, to a technique that determines whether dispensing is correctly performed in dispensing inspection with high reliability.

2. Description of the Related Art

In a dispensing pharmacy or the like, medicines are dispensed (picked) on the basis of a medical prescription issued by a doctor.

In this regard, in the dispensing pharmacy, after performing dispensing on the basis of the medical prescription, a dispensing inspection process (medicine dispensing inspection) of confirming whether the dispensing has been unmistakably performed according to the medical prescription with respect to the types and numbers of medicines is performed.

In general, such dispensing inspection is performed by confirmation based on visual observation of a pharmacist different from a pharmacist who dispenses medicines.

That is, for example, the pharmacist different from the pharmacist who dispenses medicines confirms names of dispensed medicines written on a rear surface or the like of a press through package (PTP) sheet by visual observation, and confirms the number of PTP sheets and the number of fractional medicines by visual observation to detect the number of medicines.

Thereafter, the pharmacist confirms whether the medicine names of the dispensed medicines and the number of the medicines suitably match the content of the medical prescription.

As described above, since the dispensing inspection currently depends on visual observation of a pharmacist, it cannot be said that the dispensing inspection is sufficient to prevent dispensing accidents. Further, the dispensing inspection gives a big load to the pharmacist.

In order to solve this problem, various devices that perform dispensing inspection have been proposed.

For example, JP2013-214170A discloses a medicine inspection system that performs dispensing inspection by capturing an image of a medicine that is an inspection target and analyzing the captured image.

In the medicine inspection system disclosed in JP2013-214170A, a color of a binding tool such as an elastic band is decided for each number of medicine sheets of an inspection target medicine. Further, the inspection target medicine that is a dispensing inspection target is bound by a binding tool of a color which is decided based on the number of medicine sheets, and a surface on which a barcode of each number of medicine sheets is shown is placed on a mounting table to face a camera. Then, an inspection target medicine placed on the mounting table is imaged, a medicine name of the inspection target medicine is detected from a barcode of the captured image, and the number of medicine sheets of the inspection target medicine is detected from a color of the binding tool to detect the number of medicines.

In another aspect of the medicine inspection system disclosed in JP2013-214170A, by measuring the height of the inspection target medicine placed on the mounting table instead of the color of the binding tool, the number of medicine sheets is recognized to detect the number of medicines.

Further, in the medicine inspection system disclosed in JP2013-214170A, there are an aspect in which an inspection target medicine is placed on the mounting table with a surface on which a barcode of a medicine sheet is displayed being directed upward to perform imaging of the inspection target medicine from an upper side of the mounting table, and an aspect in which a mounting table is made of a transparent material and an inspection target medicine is placed on the mounting table with a surface on which a barcode of a medicine sheet is displayed being directed downward to perform imaging of the inspection target medicine from a lower side of the mounting table.

In JP2013-214170A, according to the aspect in which the imaging is performed from the lower side of the mounting table, since a distance between the surface on which the barcode of the medicine sheet is displayed and a camera can be set uniformly regardless of the number of medicine sheets included in the inspection target medicine, it is possible to constantly acquire an image obtained by capturing the barcode with high accuracy, which is focused on the surface on which the barcode of the medicine sheet is displayed.

SUMMARY OF THE INVENTION

By using the medicine inspection system as disclosed in JP2013-214170A, it is possible to reduce load of a pharmacist in dispensing inspection.

However, in the medicine inspection system disclosed in JP2013-214170A, it is necessary to decide a color of a binging tool for each number of medicine sheets included in the inspection target medicine, and to bind the inspection target medicine using the binding tool of the color decided for each number of medicine sheets. Thus, it takes efforts to perform dispensing inspection, and there is a concern that the inspection target medicine may be bound by a wrong color binding tool.

On the other hand, in an aspect in which the height of the inspection target medicine is measured, it is necessary to measure and store the height (thickness) for each type of medicine sheet, which causes efforts.

Further, in many cases, a prescribed medicine does not include only a perfect medicine sheet but also includes a fractional medicine cut from the medicine sheet. However, in the medicine inspection system in JP2013-214170A, the number of medicines of such a fractional medicine is not considered.

In order to solve the above-mentioned problems in the related art, an object of the invention is to provide a dispensing inspection device, a dispensing inspection method, a program, and a recording medium capable of conveniently performing inspection of a medicine that is an inspection target, including a fractional medicine, with high reliability.

In order to achieve the object of the invention, according to an aspect of the invention, there is provided a dispensing inspection device of the invention comprising: a first mounting table for placing a medicine sheet and a second mounting table for placing fractional medicines cut from the medicine sheet; diffusing lighting means for irradiating the first mounting table with diffused light from a lower side of the first mounting table; first imaging means for imaging the medicine sheet placed on the first mounting table from the lower side of the first mounting table and second imaging means for imaging the medicine sheet placed on the first mounting table from a lateral side of the first mounting table; third imaging means for imaging the fractional medicines placed on the second mounting table from a lower side of the second mounting table; inclined lighting means for irradiating the second mounting table with light from a lower side of the second mounting table in a state where an optical axis thereof has an angle with respect to an optical axis of the third imaging means; medicine name detection means for detecting a medicine name of the medicine sheet using at least one of OCR and code recognition from a first image that is an image captured by the first imaging means; medicine number detection means for detecting the number of the medicine sheets from a second image that is an image captured by the second imaging means, detecting the number of fractional medicines from a third image that is an image captured by the third imaging means, and detecting a total number of medicines from the number of the medicine sheets and the number of the fractional medicines; and inspection result determination means for determining whether a medicine name and the number of medicines in acquired prescription information and the medicine name of the medicine sheets detected by the medicine name detection means and the total number of medicines detected by the medicine number detection means match each other.

In the dispensing inspection device according to this aspect of the invention, it is preferable that the dispensing inspection device further comprises side lighting means for irradiating the medicine sheet placed on the first mounting table with light from a lateral side of the first mounting table.

Further, it is preferable that an angle formed by the optical axis of the inclined lighting means and the optical axis of the third imaging means is 30° to 60°.

Further, it is preferable that the inclined lighting means emits light of which a half-width of a light intensity in an orientation distribution is 20° to 60°.

Further, it is preferable that the medicine number detection means detects the number of fractional medicines using brightness and darkness of the third image.

Further, it is preferable that the medicine number detection means detects the number of fractional medicines using a combination of a bright portion of the third image and a dark portion adjacent to the bright portion.

Further, it is preferable that the medicine number detection means performs edge detection to detect an end face of a sheet-like material from the second image, and detects the number of the medicine sheets from the second image using at least one of the shape of an end portion of the detected end face, a density between the detected end faces, a density within the detected end faces, the thickness of the detected end face, and regularity of images between the detected end faces.

Further, it is preferable that the inclined lighting means has an elongated shape, and a length of the inclined lighting means in a longitudinal direction is equal to or longer than a length, in a direction that matches the longitudinal direction of the inclined lighting means, of the imaging region set on the second mounting table.

Further, it is preferable that the first mounting table is inclined with respect to a horizontal direction.

Furthermore, it is preferable that the dispensing inspection device further comprises positioning means vertically provided with respect to the first mounting table for determining a position of the medicine sheet on the first mounting table.

According to another aspect of the invention, there is provided a dispensing inspection method comprising: capturing, in a state where a medicine sheet placed on a first mounting table with a rear surface thereof being directed downward is irradiated with diffused light from a lower side of the mounting table, a first image that is an image obtained by imaging the medicine sheet from the lower side of the first mounting table, and a second image that is an image obtained by imaging the medicine sheet from a lateral side of the first mounting table; capturing, in a state where a fractional medicine cut from a medicine sheet, which is placed on a second mounting table with a front surface thereof being directed downward, is irradiated with light from an inclined lower side of the second mounting table with respect to an optical axis for imaging, a third image that is an image obtained by imaging the fractional medicine from the lower side of the second mounting table; detecting a medicine name of the medicine sheet using at least one of OCR and code recognition from the first image, the number of the medicine sheets from the second image, the number of the fractional medicines from the third image, and a total number of medicines from the number of the medicine sheets and the number of the fractional medicines; and determining whether a medicine name and the number of medicines in acquired prescription information and the detected medicine name of the medicine sheet and the detected total number of medicines match each other.

In the dispensing inspection method according to this aspect of the invention, it is preferable that the dispensing inspection method further comprises irradiating the medicine sheet from a lateral side of the first mounting table in capturing the second image.

Further, it is preferable that in capturing the third image, an angle formed by the optical axis for capturing the third image and the optical axis of light emitted to the second mounting table is 30° to 60°.

Further, it is preferable that light emitted to the second mounting table in capturing the third image is light of which a half-width of a light intensity in an orientation distribution is 20° to 60°.

Further, it is preferable that the dispensing inspection method further comprises detecting the number of fractional medicines using brightness and darkness of the third image.

Further, it is preferable that the dispensing inspection method further comprises detecting the number of fractional medicines using a combination of a bright portion of the third image and a dark portion adjacent to the bright portion.

Further, it is preferable that the dispensing inspection method further comprises performing edge detection to detect an end face of a sheet-like material from the second image, and detecting the number of the medicine sheets from the second image using at least one of the shape of an end portion of the detected end face, a density between the detected end faces, a density within the detected end faces, the thickness of the detected end face, and regularity of images between the detected end faces.

Further, it is preferable that a light source of light emitted to the second mounting table in capturing the third image has an elongated shape, and a length thereof in a longitudinal direction is equal to or longer than a length, in a direction that matches a longitudinal direction of inclined illumination, of an imaging region set on the second mounting table.

Further, it is preferable that the first mounting table is inclined with respect to a horizontal direction.

Further, it is preferable that the first mounting table includes positioning means vertically provided with respect to the first mounting table for determining a position of the medicine sheet on the first mounting table.

According to still another aspect of the invention, there is provided a program causing a computer to execute: a step of causing first imaging means to capture a first image that is an image obtained by imaging a medicine sheet that is placed on a first mounting table and is irradiated with diffused light from a lower side, from the lower side of the first mounting table, and causing second imaging means to capture a second image that is an image captured from a lateral side of the first mounting table; a step of causing third imaging means to capture a third image that is an image obtained by imaging a fractional medicine cut from a medicine sheet that is placed on the second mounting table and is irradiated with light from a lower side in a state where an optical axis of the light is inclined with respect to an optical axis for imaging, from the lower side of the second mounting table; a step of detecting a medicine name of the medicine sheet using at least one of OCR and code recognition from the first image; a step of detecting the number of the medicine sheets from the second image, detecting the number of fractional medicines from the third image, and detecting a total number of medicines from the number of the medicine sheets and the number of the fractional medicines; and a step of determining whether a medicine name and the number of medicines in acquired prescription information and the detected medicine name of the medicine sheets and the detected total number of medicines match each other.

According to still another aspect of the invention, there is provided a computer-readable recording medium storing a program causing a computer to execute: a step of causing first imaging means to capture a first image that is an image obtained by imaging a medicine sheet that is placed on a first mounting table and is irradiated with diffused light from a lower side, from the lower side of the first mounting table, and causing second imaging means to capture a second image that is an image captured from a lateral side of the first mounting table; a step of causing third imaging means to capture a third image that is an image obtained by imaging a fractional medicine cut from a medicine sheet that is placed on the second mounting table and is irradiated with light from a lower side in a state where an optical axis of the light is inclined with respect to an optical axis for imaging, from the lower side of the second mounting table; a step of detecting a medicine name of the medicine sheet using at least one of OCR and code recognition from the first image; a step of detecting the number of the medicine sheets from the second image, detecting the number of fractional medicines from the third image, and detecting a total number of medicines from the number of the medicine sheets and the number of the fractional medicines; and a step of determining whether a medicine name and the number of medicines in acquired prescription information and the detected medicine name of the medicine sheets and the detected total number of medicines match each other.

According to the invention, it is possible to perform dispensing inspection through a simple operation with high reliability, while including a fractional medicine.

BRIEF DESCRIPTION OF THE DRAWINGS

FIG. 1 is a block diagram conceptually showing an example of a dispensing inspection device of the invention.

FIGS. 8A to 8C are diagrams conceptually illustrating examples of displays of dispensing inspection results in the dispensing inspection device shown in FIG. 1.

DESCRIPTION OF THE PREFERRED EMBODIMENTS

Hereinafter, a dispensing inspection device, a dispensing inspection method, a program and a recording medium of the invention will be described in detail on the basis of preferred embodiments shown in the accompanying drawings.

FIG. 1 is a block diagram conceptually showing an example of a dispensing inspection device of the invention that executes the dispensing inspection method of the invention.

A dispensing inspection device 10 shown in FIG. 1 is a device that supports dispensing inspection of a pharmacist by inspecting (confirming) whether medicines dispensed by the pharmacist are dispensed according to a medical prescription prescribed by a doctor in a dispensing pharmacy or the like.

The dispensing inspection device 10 basically includes a scanner 12, a processing device 14, and a display 16. In addition, the dispensing inspection device 10 may be configured so that a keyboard, a mouse, or the like for inputting an operation or a variety of information is connected thereto.

Figure 2A:
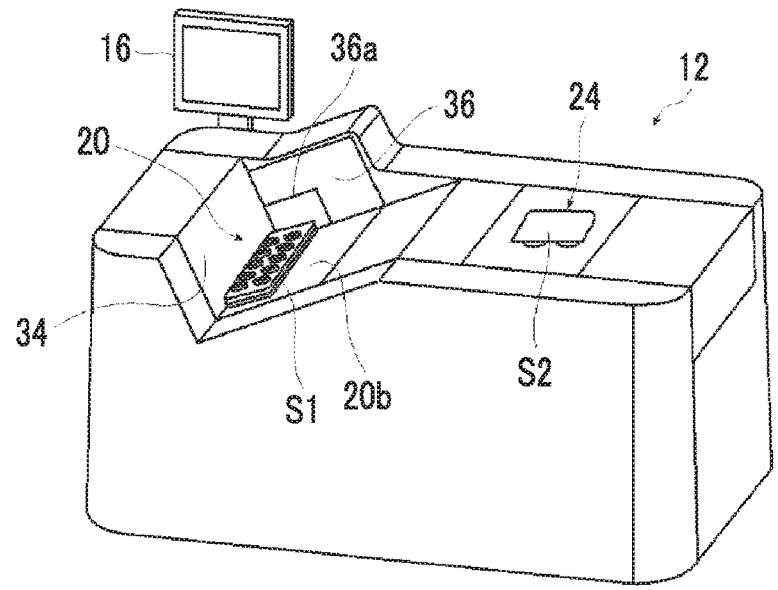
FIG. 2A is a diagram showing an appearance of a scanner of the dispensing inspection device shown in FIG. 1.
Figure 2B:
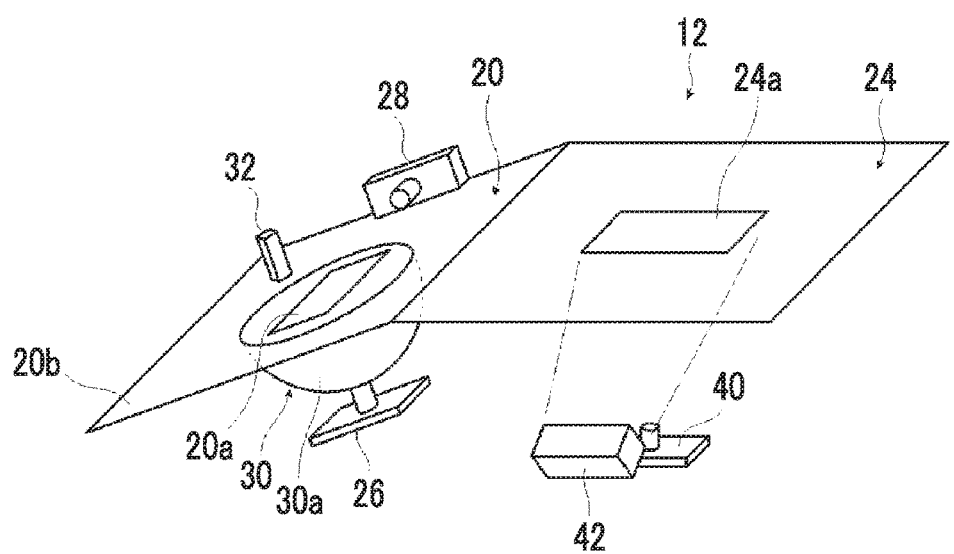
FIG. 2B is a diagram conceptually showing a configuration of the scanner of the dispensing inspection device shown in FIG. 1.

FIG. 2A is a conceptual diagram of an appearance of the scanner 12. FIG. 2B conceptually shows a configuration of the scanner 12.

The scanner 12 performs imaging of an inspection target medicine that is an inspection target, and includes a first table 20 that is a first mounting table, and a second table 24 that is a second mounting table.

The first table 20 is provided to image a press through package (PTP) sheet in the inspection target medicine that is the inspection target, on which one or plural PTP sheets are placed with a rear surface thereof being directed downward (toward the table). A transparent imaging region 20a made of a glass plate or the like is provided in the table 20.

On the other hand, a second table 24 is provided to image medicines (tablets) of fractions cut from the PTP sheet in the inspection target medicine that is the inspection target, on which fractional medicines are placed with a front surface thereof being directed downward (toward the table). A transparent imaging region 24a made of a glass plate or the like is provided in the second table 24.

The rear surface of the PTP sheet refers to a surface on a side where a medicine is extracted. On the other hand, an opposite side surface of the rear surface, that is, a surface on a side on which a convex portion due to a medicine is present refers to a front surface of the PTP sheet.

In the following description, one or plural PTP sheets are simply referred to as a sheet medicine S1. Further, in the following description, fractional medicines cut from the PTP sheet are simply referred to as a fractional medicine S2.

As shown in FIG. 2B, a first imaging device 26, a second imaging device 28, a diffusing lighting device 30, and a side lighting device 32 are provided on the first table 20.

In the first table 20 shown in FIG. 2A, as a preferred aspect, a flat abutting portion 34 and a flat abutting portion 36 are vertically provided with respect to a mounting surface 20b of the sheet medicine S1. The abutting portion 34 and the abutting portion 36 are provided to be orthogonal to each other.

The sheet medicine S1 is placed on the first table 20 with the rear surface being directed downward in a state where end faces of the PTP sheet abut on the abutting portion 34 and the abutting portion 36 and a corner of the PTP sheet is in contact with a corner formed by the abutting portion 34 and the abutting portion 36. The abutting portion 34 and the abutting portion 36 are provided so that the sheet medicine S1 is placed at an appropriate position on the imaging region 20a of the first table 20 in this state.

Thus, by setting the position of the sheet medicine S1 on the first table 20 to a predetermined position, it is possible to stably and appropriately achieve imaging of the sheet medicine S1 in the first imaging device 26 and the second imaging device 28.

The abutting portion 36 is provided with a transparent region 36a through which light is emitted from the side lighting device 32 to the sheet medicine S1 and the sheet medicine S1 is imaged by the second imaging device 28.

In the dispensing inspection device 10 of the invention, positioning means of the sheet medicine S1 is not limited to the abutting portion 34 and the abutting portion 36 as shown in the figure, and various known positioning methods in a face direction of a sheet-like material or a laminate of sheet-like materials may be used.

The dispensing inspection device 10 shown in the figure performs the positioning of the sheet medicine S1 in two orthogonal directions as a preferred aspect, but the positioning of the sheet medicine S1 may be performed in only one direction. However, as shown in the figure, when the positioning of the sheet medicine S1 is performed in two orthogonal directions, it is possible to inspect an inspection target medicine more stably and accurately.

The sheet medicine S1 having a plurality of PTP sheets placed on the first table 20 may be or may not be bound by a binding tool such as an elastic band as long as it is a laminate in which PTP sheets are layered.

The dispensing inspection device 10 is configured so that the mounting surface 20b on which the sheet medicine S1 is placed is inclined with respect to a horizontal direction on the first table 20, as a preferred aspect. Specifically, the mounting surface 20b is inclined to descend toward the abutting portion 34.

By forming the mounting surface 20b on which the sheet medicine S1 is placed to be inclined with respect to the horizontal direction so that the sheet medicine S1 placed on the mounting surface 20b drops downward, it is possible to stably and reliably position the sheet medicine S1 at a predetermined position while making the sheet medicine S1 abut on the abutting portion 34.

The first imaging device 26 and the second imaging device 28, and a third imaging device 40 (which will be described later) may use a known imaging device such as a charge coupled device camera (CCD sensor) or a complementary metal-oxide-semiconductor camera (CMOS sensor).

Further, the imaging devices may perform capturing of a color image or capturing of a monochrome image. However, in order to detect a barcode or the number of medicines based on image analysis (which will be described later) with high accuracy, for example, it is preferable that the imaging device performs capturing of a color image.

As described above, the sheet medicine S1 is placed on the first table 20 with the rear surface of the PTP sheet being directed downward. The first imaging device 26 captures a first image that is an image obtained by imaging the sheet medicine S1 placed on the first table 20 from a lower side of the first table 20.

That is, the first image is an image captured by imaging a rear surface of a PTP sheet of an inspection target medicine.

As conceptually shown in FIG. 4 (which will be described later), on a rear surface of a PTP sheet, generally, a medicine name of a medicine included in the PTP sheet is printed. Further, in recent years, it is obligatory that a barcode indicating a dispensing package unit (medicine name and the number of medicines) is attached on the PTP sheet. The barcode is generally printed on the rear surface of the PTP sheet.

The dispensing inspection device 10 performs recognition of a barcode or optical character recognition (OCR) from an image obtained by imaging the rear surface of the PTP sheet of the sheet medicine S1 to detect the medicine name of the inspection target medicine or the number of medicines included in the PTP sheet.

The diffusing lighting device 30 irradiates the imaging region 20a of the first table 20 with diffused light for imaging the sheet medicine S1 from a lower side.

In the shown example, the diffusing lighting device 30 is configured by an approximately semispherical reflector 30a of which an inner face is a diffusion reflecting surface, and a light source disposed in the reflector 30a. The light source may employ a known light source such as a light emitting diode (LED) or a halogen lamp.

The reflector 30a is disposed to cover the imaging region 20a in its opening portion, in which light emitted from the light source is diffused and reflected by the reflector 30a, and the diffused light is incident on the rear surface of the PTP sheet of the sheet medicine S placed on the imaging region 20a.

By imaging the rear surface of the PTP sheet by the first imaging device 26 in a state where the diffused light is emitted, it is possible to image the rear surface of the PTP sheet without shadow due to irregularities or the like formed on the rear surface of the PTP sheet, and thus, it is possible to accurately perform recognition of a barcode or detection of a medicine name through OCR (which will be described later).

The diffusing lighting device that emits diffused light to the imaging region 20a of the first table 20 is not limited to the example shown in the figure, and various known lighting devices that emit diffused light may be used.

The second imaging device 28 captures a second image that is an image obtained by imaging the sheet medicine S placed on the first table 20 from a lateral side of the first table 20. In the example shown in the figure, the second imaging device 28 images a side surface of the sheet medicine S1 from a back side in the figure in FIGS. 2A and 2B. That is, the second image is an image obtained by imaging a side surface of the sheet medicine S1, in other words, an end face of one PTP sheet or a plurality of laminated PTP sheets.

The dispensing inspection device 10 detects the number of PTP sheets included in the sheet medicine S1 from the image captured by imaging the side surface of the sheet medicine S1. This will be described in detail later.

In the dispensing inspection device 10 shown in the figure, as a preferred aspect, the first table 20 is provided with a side lighting device 32 that irradiates the sheet medicine S from a lateral side of the first table 20 with light. That is, the side lighting device 32 irradiates a side surface (in the figure, inclined with respect to the back side) of the sheet medicine S1 placed on the first table 20 of which the rear surface is directed downward with light.

Preferably, the side lighting device 32 irradiates a corner of the sheet medicine S (PTP sheet) positioned by the abutting portion 34 and the abutting portion 36 with light.

Figure 3:
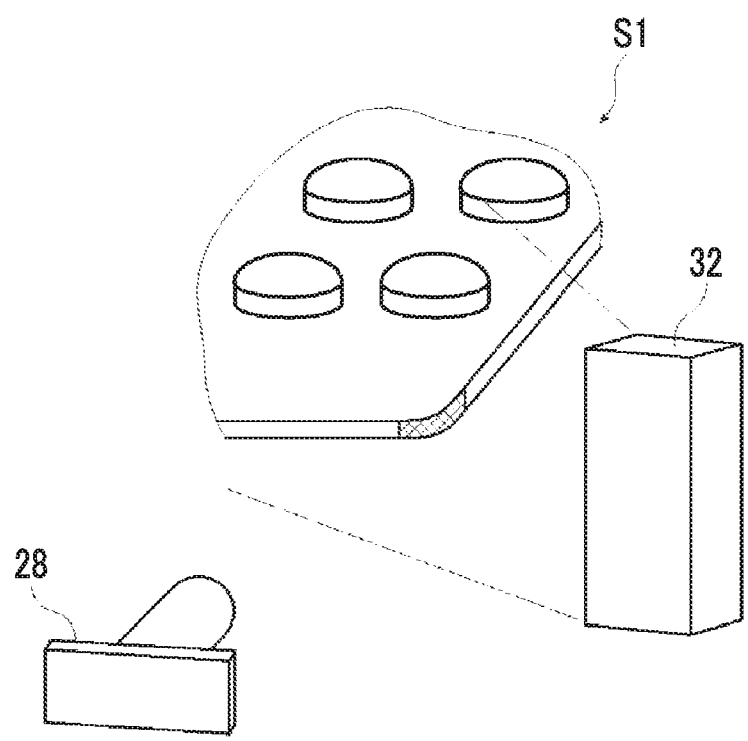
FIG. 3 is a conceptual diagram for explaining an example of an operation of the dispensing inspection device shown in FIG. 1.

The PTP sheet is generally formed of an aluminum foil and a resin material. Thus, by providing the side lighting device 32 in this way, as conceptually shown in FIG. 3, in a state where light is reflected by end faces of the PTP sheet, preferably, a corner of the end faces of the PTP sheet indicated by a mesh in FIG. 3, it is possible to image a side surface of the sheet medicine S1 by the second imaging device 28.

Thus, it is possible to use the second image as an image in which an end face of a PTP sheet of the sheet medicine S1 is emphasized, and thus, to stably perform detection of the number of PTP sheets of the sheet medicine S1 (which will be described later) with high accuracy.

In the invention, the side lighting device 32 may employ a known lighting device that includes a light source such as an LED, a halogen lamp, a fluorescent lamp, or a laser line light source in which laser light sources are provided in a flat shape, a reflector or a projector for emitting light in a predetermined direction, or the like.

The second table 24 is provided to image the fractional medicine S2 that is a medicine of a fraction cut from a PTP sheet in an inspection target medicine that is an inspection target. The fractional medicine S2 is basically placed in the imaging region 24a of the second table 24 with a front surface thereof being directed downward (toward the table).

The second table 24 includes a third imaging device 40 and an inclined lighting device 42.

The third imaging device 40 is a device that captures a third image that is an image obtained by imaging the fractional medicine S2 placed on the second table 24 from a lower side of the second table 24. That is, the third image is an image obtained by imaging a front surface of the fractional medicine S2.

The inclined lighting device 42 is a system that irradiates the imaging region 24a of the second table 24 with light for imaging the fractional medicine S2 from a lower side of the second table 24.

Here, the third imaging device 40 images the fractional medicine S2 placed on the second table 24 in a state where an optical axis thereof is orthogonal to the mounting surface on which the fractional medicine S2 is placed in the imaging region 24a. On the other hand, the inclined lighting device 42 irradiates the imaging region 24a of the second table 24 with light in a state where an optical axis thereof is inclined with respect to the optical axis of the third imaging device 40.

That is, the third image is an image obtained by imaging the front surface of the fractional medicine S2 in a state where light is emitted in an inclined direction with respect to the optical axis (imaging direction) of the third imaging device 40. In other words, the third image is an image obtained by imaging the front surface of the fractional medicine S2 in a state where the fractional medicine S2 is irradiated with light in an inclined direction.

A convex portion due to a medicine is present on a front surface of a PTP sheet.

Accordingly, in a state where the front surface of the fractional medicine S2 is directed downward and a sheet surface is not irradiated with ambient light such as an indoor lighting to be darkened, by irradiating the front surface of the fractional medicine S2 with light in an inclined direction, shadow due to the convex portion due to the medicine is formed on the front surface of the fractional medicine S2. On the other hand, since the medicine diffuses and reflects the light, even in a case where the light is incident in an inclined direction, the light reflected by the medicine is incident on the third imaging device 40, so that the medicine is taken to be bright. That is, in the third image obtained by imaging the front surface of the fractional medicine S2 by inclined irradiation of light, a bright portion due to the medicine and a dark portion due to the shadow of the medicine are present to be adjacent to each other at the position of the medicine.

The dispensing inspection device 10 of the invention detects the number of medicines included in the fractional medicine S2 using the brightness and darkness of the third image due to the shadow of the medicine. This will be described in detail later.

Further, the PTP sheet is formed of aluminum foil, or the like. Thus, a front surface of the PTP sheet has some degree of light reflectivity. In a case where light reflected from a flat portion of the PTP sheet is incident on the third imaging device 40, the light becomes interfering light of a ghost image or the like of a light source, which lowers image quality of the third image. The lowering of the image quality of the third image lowers detection accuracy of the number of fractional medicines included in the fractional medicine S2 (which will be described later).

On the other hand, by imaging the flat portion of the fractional medicine S2 from a front side in a state where the fractional medicine S2 is irradiated with light for imaging in an inclined direction, it is possible to prevent light reflected from a flat portion of a sheet of the fractional medicine S2 from being incident on the third imaging device 40, to stably capture the third image with high image quality. Further, since the light reflected from the flat portion of the sheet of the fractional medicine S2 is reflected in a direction different from a direction toward the third imaging device 40 and the medicine diffuses and reflects the light, it is possible to particularly brighten the medicine in the third image.

An angle of the optical axis of the inclined lighting device 42 with respect to the optical axis of the third imaging device 40, that is, a light irradiation direction of the inclined lighting device 42 with respect to the optical axis of the third imaging device 40 may be set by appropriately setting an angle or a distance at which an entire region of the imaging region 24a can be irradiated with light from the inclined lighting device 42 with a suitable light intensity.

Here, in a case where the angle of the optical axis of the inclined lighting device 42 with respect to the optical axis of the third imaging device 40 is excessively small, the shadow due to the medicine is not sufficiently generated. Contrarily, in a case where the angle of the optical axis of the inclined lighting device 42 with respect to the optical axis of the third imaging device 40 is excessively large, the shadow becomes unnecessarily large, which causes difficulties in detection of the shadow.

In consideration of the above-described points, the light irradiation direction of the inclined lighting device 42 is set so that the angle formed by the optical axis of light emitted by the inclined lighting device 42 and the optical axis of the third imaging device 40 is preferably 30° to 60°, and more preferably 45° to 60°.

By setting the light irradiation direction of the inclined lighting device 42 in the above-mentioned range, it is possible to suitably form the shadow due to the medicine of the fractional medicine S2, to thereby accurately detect the number of fractional medicines.

A distance between the inclined lighting device 42 and the second table 24 may be set by appropriately setting a distance at which the entire region of the imaging region 24a is irradiated with the light from the inclined lighting device 42, in accordance with the irradiation angle of the inclined lighting device 42, the size of the inclined lighting device 42, the directionality or intensity of light to be emitted, or the like.

It is preferable that the light emitted by the inclined lighting device 42 has some degree of directionality. As the light of the inclined lighting device 42 has the directionality, it is possible to suitably form the shadow of the medicine, to thereby accurately detect the number of fractional medicines.

According to review of the inventors of the invention, the light emitted by the inclined lighting device 42 is set so that its half-width (full width at half maximum) in an orientation distribution (an orientation curve) is preferably 20° to 60° (±10° to 30°), and more preferably 20° to 40° (±10° to 20°). The half-width in the orientation distribution refers to, in other words, an angle at which the intensity of light (radiation intensity (light intensity)) in an orientation distribution becomes a half of the front (on an optical axis).

By setting the half-width of the light emitted by the inclined lighting device 42 to 20° to 60°, it is possible to suitably obtain an effect of inclined incidence of light for imaging onto the fractional medicine S2 and to more suitably form shadow due to the medicine, to thereby accurately detect the number of fractional medicines.

The inclined lighting device 42 may employ various known lighting devices formed by a light source such as an LED or a fluorescent lamp, a reflector, a lens for adjusting orientation or the like of light to be emitted, or the like.

Here, it is preferable that the inclined lighting device 42 is an elongated lighting device such as a lighting device that includes one column LED or plural column LEDs that are arranged in one direction, or a lighting device that uses a fluorescent lamp. Particularly, it is preferable that the inclined lighting device 42 is configured so that the length thereof in a longitudinal direction is equal to or longer than a length, in a direction (hereinafter, referred to as the same direction) that matches the longitudinal direction of the inclined lighting device 42, of the imaging region 24a of the second table 24.

The intensity of the light emitted by the lighting device becomes lower as it goes toward an end portion in the light diffusion direction. Thus, by setting the inclined lighting device 42 to have an elongated shape and setting the length thereof in the longitudinal direction to be equal to or longer than the length of the imaging region 24a in the same direction, it is possible to appropriately irradiate the entire region of the imaging region 24a with light, and thus, it is possible to appropriately and stably detect the number of medicines of the fractional medicine S2 regardless of the mounting position of the fractional medicine S2 in the imaging region 24a.

The display 16 is a known display (display device) configured by a liquid crystal display (LCD) or the like.

The display 16 displays a variety of information, or the like, relating to images captured by the first imaging device 26 to the third imaging device 40, results of dispensing inspections, operations of the dispensing inspection device 10, or the like. Further, in the example shown in the figure, as an example, the display 16 is a so-called touch panel, and displays a button, a menu, an operation instruction, or the like for operating the dispensing inspection device 10.

The display of the images on the display 16 is controlled by a display control unit 62 of the processing device 14.

The processing device 14 includes an image acquisition unit 50, an image processing unit 52, a detection unit 54, an inspection result determination unit 56, a lighting control unit 58, a storage unit 60, the display control unit 62, and a control unit 64. The processing device 14 is configured using a computer, for example. The control unit 64 is a unit that controls an entire operation or the like of the dispensing inspection device 10.

Further, the operation unit 46 is provided in the dispensing inspection device 10. In the example shown in the figure, the display 16 is a touch panel, and the display 16 forms the operation unit 46.

Hereinafter, through the description of operations of the dispensing inspection device 10, the processing device 14, the dispensing inspection device 10, and the dispensing inspection method of the invention will be described in detail. A program of the invention is a program for causing a computer to execute the following operations. Further, a recording medium of the invention is a computer-readable recording medium on which the program of the invention is recorded.

First, the fractional medicine S2 is excluded from an inspection target medicine by a pharmacist or the like, the sheet medicine S1 is positioned by the abutting portion 34 and the abutting portion 36 and is placed in the imaging region 20a of the first table 20 with a rear surface of a PTP sheet being directed downward, and the fractional medicine S2 is placed in the imaging region of the second table 24 with a front surface thereof being directed downward.

Further, information on a medical prescription from a reception computer RC is supplied to the inspection result determination unit 56 through a network based on NSIPS (registered trademark) (New Standard Interference of Pharmacy-system Specifications: dispensing system prescription IF sharing specifications). The information on the medical prescription may be acquired through OCR by optically reading the medical prescription by a scanner or the like.

The information (reception data) on the medical prescription includes medicine names of prescribed medicines and the number of medicines. The inspection result determination unit 56 detects the medicine names of the prescribed medicines and the number of medicines from the information on the supplied medical prescription.

Then, if an inspection start instruction is input, the diffusing lighting device 30, the side lighting device 32, and the inclined lighting device 42 are driven by an instruction of the lighting control unit 58. Further, the diffusing lighting device 30 irradiates a rear surface of the sheet medicine S1, the side lighting device 32 irradiates a side surface of the sheet medicine S1, particularly, a corner thereof with light, and the inclined lighting device 42 irradiates a front surface of the fractional medicine S2 with light in an inclined direction, respectively.

A method for detecting that the sheet medicine S and the fractional medicine S2 are placed on corresponding tables from images captured by the first imaging device 26 and/or the second imaging device 28, and the third imaging device 40, and automatically starting the dispensing inspection may be used.

Then, the first imaging device 26, the second imaging device 28, and the third imaging device 40 capture images. As described above, the first imaging device 26 captures a first image obtained by imaging a rear surface of the PTP sheet of the sheet medicine S1, the second imaging device 28 captures a second image obtained by imaging a side surface of the sheet medicine S1, and the third imaging device 40 captures a third image obtained by imaging a front surface of the fractional medicine S2 from a front side, respectively.

The first image captured by the first imaging device 26, the second image captured by the second imaging device 28, and the third image captured by the third imaging device 40 are all acquired by the image acquisition unit 50, and then, are supplied to the image processing unit 52.

The image processing unit 52 performs predetermined image processing such as color correction, gradation correction, noise removal, or region mask processing with respect to the first image, the second image, and the third image.

Here, preferably, the image processing unit 52 supplies the processed first image, second image and third image to the display control unit 62. The display control unit 62 displays the first image, the second image, and the third image on the display 16.

In the invention, the images displayed on the display 16 are not limited to all of the first image, the second image, and the third image, and for example, any one of the first image, the second image, and the third image may be displayed, or appropriately selected two images, for example, the first image and the third image may be displayed. Further, a pharmacist or the like may select an image to be displayed.

However, in order to accurately perform dispensing inspection, it is preferable to display all of the first image, the second image, and the third image, and in order to visually observe the number of medicines of the fractional medicine S2, it is preferable to display at least the third image obtained by imaging the front surface of the fractional medicine S2.

The image processing unit 52 supplies the images subjected to the image processing to the detection unit 54 and the storage unit 60.

The storage unit 60 stores the first image, the second image, and the third image in association.

The detection unit 54 analyzes the first image, the second image, and the third image supplied from the image processing unit 52, to thereby detect a medicine name of an inspection target medicine including the sheet medicine S1 and the fractional medicine S2 and the number of medicines.

The detection unit 54 detects the medicine name of the inspection target medicine from the first image obtained by imaging the rear surface of the PTP sheet of the sheet medicine S1, imaged by the first imaging device 26.

Figure 4:
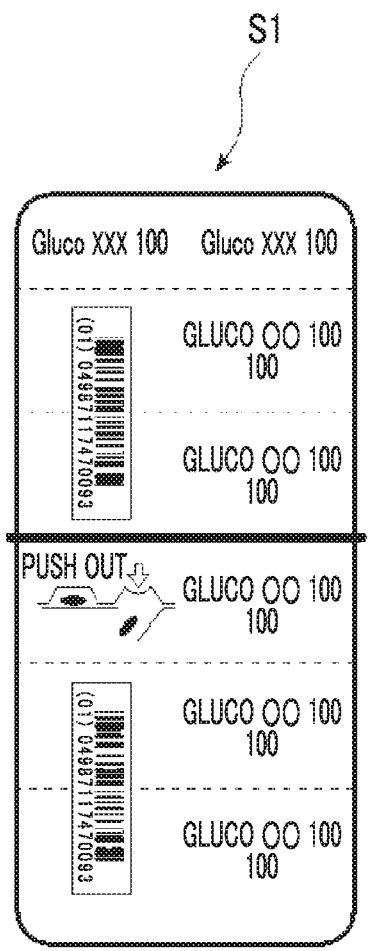
FIG. 4 is a conceptual diagram of an example of a first image obtained by imaging a rear surface of a medicine sheet.

FIG. 4 conceptually shows an example of the first image. As shown in FIG. 4, medicine names of medicines included in a PTP sheet are generally printed on a rear surface of the PTP sheet. Further, in recent years, it is obligatory that a barcode indicating a dispensing package unit (medicine name and the number of medicines) is attached on the PTP sheet.

The detection unit 54 analyzes the first image to extract a barcode, and in a case where the barcode can be extracted, the detection unit 54 recognizes the barcode (code in the dispensing package unit) (reads barcode). The extraction and recognition of the barcode may be performed by a known method.

In general, a dispensing pharmacy has a medicine database DB that stores information on a dispensing package unit of a medicine to be handled (medicine name, the number of medicines), drug effects, a dosing time, and a drug price. The detection unit 54 retrieves the medicine database DB using the recognized barcode to search for a PTP sheet in the dispensing package unit corresponding to the recognized barcode, and detects a medicine name of the PTP sheet and the number of medicines included in one sheet.

In the dispensing inspection device of the invention, a code recognition method is not limited to a barcode, and for example, various known code recognition methods such as a two-dimensional barcode may be employed.

In a case where the barcode cannot be extracted from the first image, the detection unit 54 analyzes the first image through OCR, to thereby recognize characters written on a rear surface thereof and to detect a medicine name. The OCR may be performed by a known method.

The detection of the medicine name from the first image may be performed by using the method through OCR and the method through code recognition together. Further, in a case where the method through OCR and the method through code recognition are used together, in a case where a medicine name through OCR and a medicine name through code recognition are different from each other, it may be determined that an error occurs.

Here, in a case where the barcode cannot be detected from the first image, the number of medicines of a medicine included in the PTP sheet becomes unclear.

In this case, a display for inputting the number of medicines included in the PTP sheet is performed on the display 16, and then, the number of medicines of the PTP sheet is acquired. Alternatively, a reference table indicating a relationship between a medicine name and the number of medicines may be created with respect to a PTP sheet on which a barcode is not recorded, and the number of medicines of the PTP sheet may be acquired.

Further, the number of medicines of a general PTP sheet is 10. Accordingly, a medicine name having a PTP sheet in which the number of medicines is not 10 is stored, and in a case where a detected medicine name is the medicine name that is not stored, the number of medicines of the PTP sheet is set to be 10. On the other hand, in a case where the detected medicine name is the stored medicine name, a display for inputting the number of medicines included in the PTP sheet may be performed on the display 16, and then, the number of medicines of the PTP sheet may be acquired. Alternatively, the same reference table as the above-mentioned reference table may be created with respect to a medicine of which a medicine name is stored, and then, the number of medicines of the PTP sheet may be acquired using the reference table.

There is a case where it is not possible to appropriately recognize a barcode or a character string from the first image such as a case where the sheet medicine S1 is placed on the first table 20 with the front surface of the PTP sheet being directed downward, for example. In this case, the dispensing inspection device 10 outputs occurrence of an error through display on the display 16, for example, places the sheet medicine S1 again, and prompts dispensing inspection through visual observation, confirmation of the sheet medicine S1, or the like. Further, even in a case where a PTP sheet in the dispensing package unit corresponding to the recognized barcode is not present in the medicine database DB, the dispensing inspection device 10 outputs an error in a similar manner.

Further, the detection unit 54 detects the number of PTP sheets included in the sheet medicine S1 from the second image obtained by imaging the side surface of the sheet medicine S1, imaged by the second imaging device 28.

As an example, the detection unit 54 performs edge detection of the second image, calculates a straight line through Hough conversion, and detects an end face of a PTP sheet.

Here, as described above, by illuminating a side surface of the sheet medicine S1, particularly, a corner, by the side lighting device 32, it is possible to enhance the accuracy of detection of the end face of the PTP sheet.

Figure 5A:
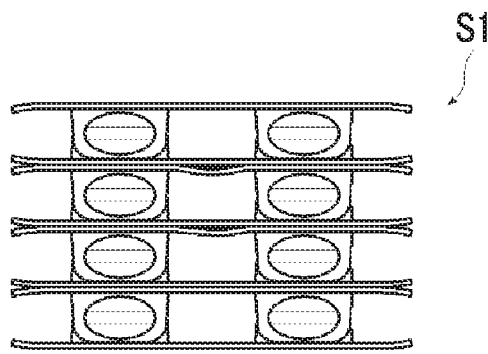
FIGS. 5A and 5B are conceptual diagrams of an example of a second image obtained by imaging a side surface of an inspection target medicine.
Figure 5B:
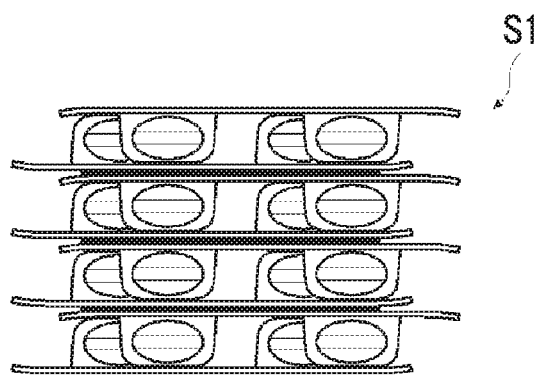

FIGS. 5A and 5B conceptually show an example of the second image.

As shown in FIGS. 5A and 5B, with respect to end faces of PTP sheets, there are many cases where end portions are in a state of being warped. Accordingly, in the detected end portions of the end faces, by counting the number of the end faces, it is possible to detect the number of PTP sheets. As shown in FIG. 5A, even in a case where one end face is seen at a central portion thereof, by observing end portions of the end faces, it is possible to determine whether two PTP sheets are laminated with rear surfaces thereof being fitted to each other or one PTP sheet is present, to thereby detect the number of PTP sheets included in the sheet medicine S1.

Further, as shown in FIG. 5B, even in a state where two PTP sheets are laminated with rear surfaces thereof being fitted to each other, in many cases, a gap is present between the PTP sheets. Since the gap between the PTP sheets becomes shadow, the gap has low brightness compared with end faces of the PTP sheets formed of aluminum foil or resin. Accordingly, in a case where there is a dark portion between the detected end faces, it is possible to determine that two PTP sheets are in a state of being laminated with rear surfaces thereof being fitted to each other.

Alternatively, even in a state where two PTP sheets are laminated with rear surfaces thereof being fitted to each other and are in close contact with each other, as shown in FIG. 5A, there are many cases where they are partially spaced from each other. The spaced portion also becomes shadow, and thus, has low brightness. Accordingly, even though it seems like one end face of the PTP sheet is seen, in a case where a dark portion is present inside a detected end face, it is possible to determine that two PTP sheets are laminated with rear surfaces thereof being fitted to each other.

Figure 6A:
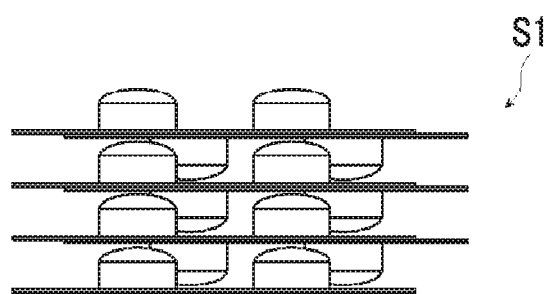
FIGS. 6A and 6B are conceptual diagrams of another example of a second image obtained by imaging a side surface of an inspection target medicine.
Figure 6B:
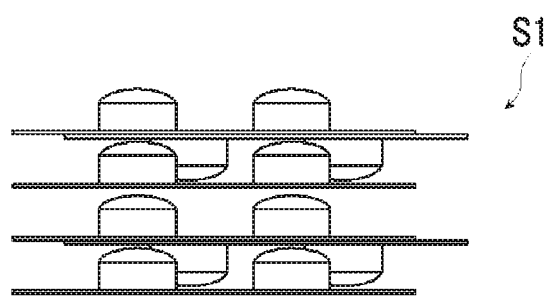

FIGS. 6A and 6B conceptually show another example of the second image obtained by imaging a side surface of the sheet medicine S1.

In dispensing, in order to make the thickness of prescribed medicines thin, there are many cases where front surfaces of two PTP sheets are fitted to each other so that two PTP sheets are laminated. Further, there are also many cases where two PTP sheets of which front surfaces are fitted to each other may deviate from each other in a planar direction.

Here, as shown in FIGS. 6A and 6B, in a case where PTP sheets are laminated in a state of deviating from each other in a planar direction, even though two PTP sheets of which rear surfaces are fitted to each other are seen to have one end face, the thickness is different between a central portion and end portions. Accordingly, the detected thickness of the end face is different between the central portion and the end portions, it is possible to determine that two PTP sheets are laminated with rear surfaces thereof being fitted to each other.

Further, in a case where front surfaces of two PTP sheets are fitted to each other so that the PTP sheets are laminated, medicines are present between detected end faces. Here, in a case where a missing is not present between PTP sheets of which front surfaces are fitted to each other, as shown in FIG. 6A, arrangements of medicines are the same between detected end faces. On the other hand, in a case where there is a missing in PTP sheets, as shown in FIG. 6B, in a portion where the missing is present in the PTP sheets, an arrangement of medicines is different from that between other end faces.

Accordingly, as a result of analysis of detected end faces is analyzed, in a case where an arrangement of medicines has an end face that is different from that of a different arrangement, that is, in a case where regularity of images is broken between the detected plural end faces, it may be considered that there is a missing of a PTP sheet between end faces having different arrangements of medicines.

The detection unit 54 analyzes the second image in this way, and detects the number of PTP sheets included in the sheet medicine S1 using at least one of the shape of end portions of detected end faces, the density between the detected end faces, the density within the detected end faces, the thicknesses of the detected end faces, and regularity of images between the detected end faces.

In a case where it is not possible to appropriately detect the number of PTP sheets included in the sheet medicine S1 from the second image, the detection unit 54 outputs occurrence of an error through display on the display 16, for example, places the sheet medicine S1 again, and prompts dispensing inspection through visual observation, confirmation of the sheet medicine S1, or the like.

Further, the detection unit 54 detects the number of fractional medicines from the third image obtained by imaging the fractional medicine S2 placed on the second table 24 with a front surface thereof being directed downward.

Figure 7A:
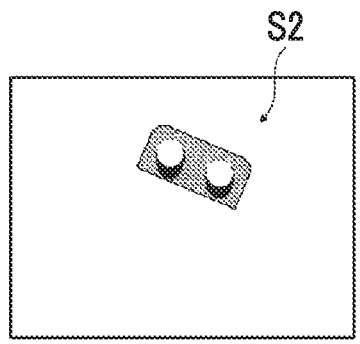
FIGS. 7A to 7F are conceptual diagrams for explaining an operation of the invention.

FIG. 7A conceptually shows an example of the third image.

Figure 7B:
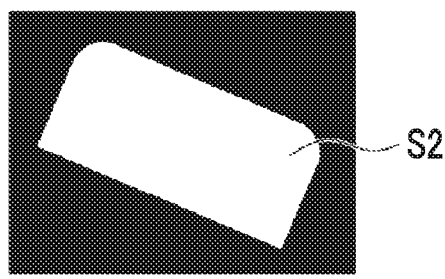

The detection unit 54 analyzes the third image as shown in FIG. 7A, and extracts a sheet region of the fractional medicine S2, as conceptually shown in FIG. 7B. The extraction of the sheet region may be performed by known methods such as background subtraction, edge detection, extraction using continuity of images (pixels), or the like.

Figure 7C:
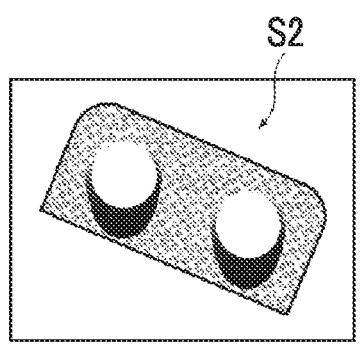

As described above, the third image is captured by emitting light for imaging in an inclined direction with respect to an optical axis of the third imaging device 40 that captures the third image by the inclined lighting device 42. Thus, shadow due to a convex portion of a medicine is generated in the sheet region, as conceptually shown in FIG. 7C. Further, as described above, since a medicine diffuses and reflects light while a PTP sheet is created using aluminum foil or the like and reflects inclined incident light in a direction different from a direction toward the third imaging device 40, the light reflected by the medicine is incident on the third imaging device 40. Thus, the medicine becomes bright in the third image.

Figure 7D:
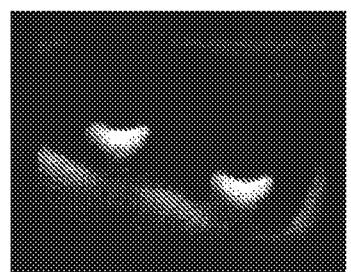

That is, in the third image, a bright medicine and shadow due to a convex portion of the medicine are imaged to be adjacent to each other. Accordingly, the detection unit 54 extracts the bright portion and the dark portion of the image, as a characteristic region, in the extracted sheet region, as conceptually shown in FIG. 7D.

Figure 7E:
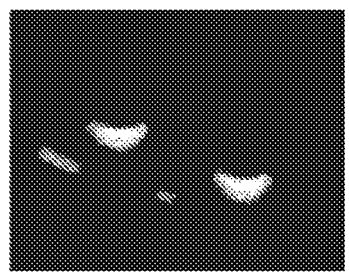

Further, as shown in FIG. 7E, the detection unit 54 detects a region where a bright portion and a dark portion are adjacent to each other as a medicine candidate, in the extracted sheet region.

Here, in the vicinity of an end portion of the sheet region, a medicine cannot be present. Further, an unusually large bright portion or an unusually small bright portion is not present in a medicine. Accordingly, even in a case where the bright portion and the dark portion are adjacent to each other, in the case of a region positioned in the vicinity of an end portion in the sheet region, or in the case of a region in which the size of a bright portion is not suitable, such a region is not extracted as a medicine candidate.

Figure 7F:
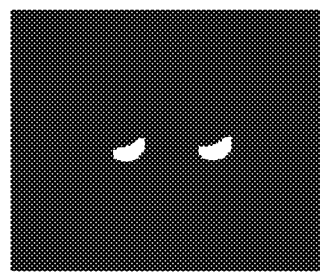

After the medicine candidate is extracted, the detection unit 54 rotates the third image so that an arrangement direction of the medicine candidates becomes a predetermined direction, as shown in FIG. 7F.

The fractional medicine S2 is cut from a PTP sheet. That is, in the fractional medicine S2, medicines are regularly arranged. Accordingly, in the medicine candidates that are arranged in the predetermined direction, a portion that deviates from the regular arrangement does not represent a medicine.

The detection unit 54 finally extracts medicines from the fractional medicine S2 by excluding medicine candidates that deviate from a regular arrangement in the third image that is rotated so that the arrangement direction of the medicines becomes the predetermined direction, and detects the number of medicines included in the fractional medicine S2.

In a case where it is not possible to appropriately detect the number of medicines of the fractional medicine S2 from the third image such as a case where the fractional medicine S2 is placed on the second table with its rear surface being directed downward, for example, the detection unit 54 outputs occurrence of an error through display on the display 16, for example, places the fractional medicine S2 again, and prompts dispensing inspection through visual observation, recognition of the fractional medicine S2, or the like.

The detection unit 54 detects a medicine name of the sheet medicine S1 from the first image and the number of medicines of PTP sheets included in the sheet medicine S1, detects the number of PTP sheets included in the sheet medicine S1 from the second image, and detects the number of medicines included in the fractional medicine S2 from the third image, and then, calculates the number of medicines (total number of medicines) of an inspection target medicine including the sheet medicine S1 and the fractional medicine S2, from the number of PTP sheets of the sheet medicine S1, the number of medicines included in the PTP sheets, and the number of medicines included in the fractional medicine S2.

Then, the detection unit 54 supplies the medicine name of the inspection target medicine and the number of medicines that are detection results to the inspection result determination unit 56, the storage unit 60, and the display control unit 62. The storage unit 60 stores the medicine name and the number of medicines supplied from the detection unit 54 in association with the first image, the second image, and the third image that are previously supplied from the image processing unit 52.

The inspection result determination unit 56 compares a medicine name and the number of medicines of a prescribed medicine with the medicine name and the number of medicines of the inspection target medicine supplied from the detection unit 54 from information on a medical prescription supplied from the reception computer RC to determine whether the medicine name and the number of medicines of the inspection target medicine detected by the dispensing inspection device 10 match those in the supplied medical prescription.

In a case where the medicine name and the number of medicines of the inspection target medicine supplied from the detection unit 54 match those in the medical prescription, the inspection result determination unit 56 gives an instruction to the display control unit 62 to perform a display (O pass) indicating that an inspection result is appropriate, as conceptually shown in FIG. 8A.

In a case where the number of medicines of the inspection target medicine supplied from the detection unit 54 is larger than the number of medicines of the prescribed medicine, the inspection result determination unit 56 gives an instruction to the display control unit 62 to perform a display (X excess) indicating that the inspection result is not appropriate and the number of medicines is excessively large, as conceptually shown in FIG. 8B.

In a case where the number of medicines of the inspection target medicine supplied from the detection unit 54 is smaller than the number of medicines of the prescribed medicine, the inspection result determination unit 56 gives an instruction to the display control unit 62 to perform a display (X shortage) indicating that the inspection result is not appropriate and the number of medicines is insufficient, as conceptually shown in FIG. 8C.

Further, in a case where the medicine name of the prescribed medicine and the medicine name of the inspection target medicine supplied from the detection unit 54 are different from each other, the inspection result determination unit 56 gives an instruction to the display control unit 62 to perform a display indicating that the medicine names are different from each other.

The display control unit 62 causes the display 16 to execute a display based on a determination result.

Here, in the display shown in FIG. 8C corresponding to a case where the inspection target medicine is insufficient, a display of "(additional input?)" corresponds to a case where imaging of the third image is dividedly performed two times.

In dispensing, for example, in a case where the number of medicines is 21, instead of a method for obtaining two PTP sheets and one fractional tablet, for example, a method for releasing one PTP sheet, five fractional tablets, and six fractional tablets are used. Thus, a dispensing pharmacy prevents accidental ingestion of taking a medicine without extraction from a PTP sheet.

In such case, it is necessary to image two fractional medicines S2. The display of "(additional input?)" is shown in FIG. 8C corresponds thereto, and is a display for asking and confirming the presence and absence of additional input of fractions, that is, additional imaging of the third image.

In the dispensing inspection device 10 of the invention, in a case where there are two fractional medicines S2, imaging of the third image may be performed two times corresponding to each fractional medicine S2, or two fractional medicines S2 may be placed on the second table 24 and may be imaged into one third image to detect the number of fractional medicines as described above.

For example, in a case where two fractional medicines S2 can be placed on the second table 24 in accordance with the size of the imaging region 24a of the second table 24 and the size of the fractional medicine S2, two fractional medicines S2 are imaged into one third image, and in a case where two fractional medicines S2 cannot be placed on the second table 24, the third image is dividedly captured two times.

Further, in the dispensing inspection device 10 of the invention, in a case where two fractional medicines S2 are simultaneously imaged, a pharmacist or the like may input the fact through the operation unit 46. Alternatively, a pharmacist or the like may input imaging of one fractional medicine S2, one-time imaging of two fractional medicines S2, or two-time imaging of two fractional medicines S2 through the operation unit 46.

As described above, according to the dispensing inspection device 10 of the invention, by placing the sheet medicine S1 on the first table 20 with a rear surface of a PTP sheet being directed downward while excluding the fractional medicine S2 from a dispensed inspection target medicine and placing the fractional medicine S2 on the second table with a front surface thereof being directed downward, it is possible to determine whether a medicine name and the number of medicines of a prescribed inspection target medicine are appropriate while including the number of medicines of fractional medicines, by only giving an instruction of inspection starting, or in an automatic manner.

Further, it is not necessary to use binding tools such as elastic bands that are classified according to the number of PTP sheets of an inspection target medicine. In addition, since the dispensing inspection device 10 of the invention captures an image of an inspection target medicine to detect the number of PTP sheets through image analysis, it is not necessary to recognize the thickness for each PTP sheet, differently from a case where the number of PTP sheets is calculated from the thickness of an inspection target medicine.

Thus, according to the dispensing inspection device 10 of the invention, it is possible to greatly reduce load of dispensing inspection of a pharmacist in a dispensing pharmacy or the like.

The inspection result determination unit 56 supplies a determination result indicating whether a prescribed inspection target medicine is appropriate or not, that is, an inspection result to the storage unit 60.

The storage unit 60 stores the supplied inspection result in association with the first image, the second image, and the third image supplied from the image processing unit 52.

The dispensing inspection device 10 in the example shown in the figure stores the first image, the second image, the third image, the medicine name and the number of medicines that are captured, and the inspection result (determination result) in the storage unit 60 in association.

In this way, by storing the images of the inspection target medicine, the medicine name and the number of medicines, and the inspection result in association, even in a case where it is necessary to confirm medicines provided to a patient someday, it is possible to show the images, the medicine name, the number of medicines, and the inspection result, to thereby appropriately handle the necessity.

The images of the inspection target medicine, the medicine name, the number of medicines, the inspection result, and the like may be stored in a local personal computer, a network cloud server, or the like, instead of the storage unit 60 of the dispensing inspection device 10 or in addition to the storage unit 60 of the dispensing inspection device 10.

The invention is not limited to a configuration in which the images obtained by imaging the inspection target medicine, the medicine name, the number of medicines, and the inspection result are all stored. For example, only the inspection result and the images may be stored, only the medicine name, the number of medicines and the inspection result may be stored, or only the medicine name, the number of medicines and the images may be stored. Alternatively, any information may not be stored.

Hereinbefore, the dispensing inspection device, the dispensing inspection method, the program, and the recording medium of the invention have been described in detail, but the invention is not limited to the above-described examples, and various improvements or modifications may be made in a range without departing from the concept of the invention.

The invention can be appropriately used in supporting of dispensing inspection in a pharmacy or the like.

EXPLANATION OF REFERENCES

10: dispensing inspection device
12: scanner
14: processing device
16: display
20: first table
24: second table
26: first imaging device
28: second imaging device
30: diffusing lighting device
32: side lighting device
34, 36: abutting portion
40: third imaging device
42: inclined lighting device
46: operation unit
50: image acquisition unit
52: image processing unit
54: detection u nit
56: inspection result determination unit
58: lighting control unit
60: storage unit
62: display control unit
64: control unit
S1: sheet medicine
S2: fractional medicine
DB: medicine database
RC: reception computer

What is claimed is:

1. A dispensing inspection device comprising:
a first mounting table for placing one or more medicine sheets and a second mounting table for placing fractional medicines cut from the one or more medicine sheets;
diffusing lighting means for irradiating the first mounting table with diffused light from a lower side of the first mounting table;
first imaging means for imaging the one or more medicine sheets placed on the first mounting table from the lower side of the first mounting table and second imaging means for imaging the one or more medicine sheets placed on the first mounting table from a lateral side of the first mounting table;
third imaging means for imaging the fractional medicines placed on the second mounting table from a lower side of the second mounting table;
inclined lighting means for irradiating the second mounting table with light from a lower side of the second mounting table in a state where an optical axis thereof has an angle with respect to an optical axis of the third imaging means;
medicine name detection means for detecting a medicine name of the one or more medicine sheets using at least one of Optical Character Recognition (OCR) and code recognition from a first image captured by the first imaging means;

medicine number detection means for detecting the number of the one or more medicine sheets from a second image captured by the second imaging means, detecting the number of fractional medicines from a third image captured by the third imaging means, and detecting a total number of medicines from the number of the one or more medicine sheets and the number of the fractional medicines; and inspection result determination means for determining whether a medicine name and a number of medicines in acquired prescription information and the medicine name of the one or more medicine sheets detected by the medicine name detection means and the total number of medicines detected by the medicine number detection means match each other.

2. The dispensing inspection device according to claim 1, further comprising: side lighting means for irradiating the one or more medicine sheets placed on the first mounting table with light from a lateral side of the first mounting table.

3. The dispensing inspection device according to claim 1, wherein an angle formed by the optical axis of the inclined lighting means and the optical axis of the third imaging means is 30° to 60°.

4. The dispensing inspection device according to claim 1, wherein the inclined lighting means emits light of which a half-width of a light intensity in an orientation distribution is 20° to 60°.

5. The dispensing inspection device according to claim 1, wherein the medicine number detection means detects the number of fractional medicines using brightness and darkness of the third image.

6. The dispensing inspection device according to claim 5, wherein the medicine number detection means detects the number of fractional medicines using a combination of a bright portion of the third image and a dark portion adjacent to the bright portion.

7. The dispensing inspection device according to claim 1, wherein the medicine number detection means performs edge detection to detect an end face of a sheet-like material from the second image, and detects the number of the one or more medicine sheets from the second image using at least one of the shape of an end portion of the detected end face, a density between the detected end faces, a density within the detected end faces, the thickness of the detected end face, and regularity of images between the detected end faces.

8. The dispensing inspection device according to claim 1, wherein the inclined lighting means has an elongated shape, and a length of the inclined lighting means in a longitudinal direction is equal to or longer than a length, in a direction that matches the longitudinal direction of the inclined lighting means, of the imaging region set on the second mounting table.

9. The dispensing inspection device according to claim 1, wherein the first mounting table is inclined with respect to a horizontal direction.

10. The dispensing inspection device according to claim 1, further comprising: positioning means vertically provided with respect to the first mounting table for determining a position of the one or more medicine sheets on the first mounting table.

11. A dispensing inspection method comprising:

capturing, in a state where one or more medicine sheets placed on a first mounting table with a rear surface thereof being directed downward is irradiated with diffused light from a lower side of the mounting table, a first image obtained by imaging the one or more medicine sheets from the lower side of the first mounting table, and a second image obtained by imaging the one or more medicine sheets from a lateral side of the first mounting table;

capturing, in a state where fractional medicines cut from the one or more medicine sheets are placed on a second mounting table with a front surface thereof being directed downward and are irradiated with light from an inclined lower side of the second mounting table with respect to an optical axis for imaging, a third image obtained by imaging the fractional medicines from the lower side of the second mounting table;

detecting a medicine name of the one or more medicine sheets using at least one of Optical Character Recognition (OCR) and code recognition from the first image, the number of the one or more medicine sheets from the second image, the number of the fractional medicines from the third image, and a total number of medicines from the number of the one or more medicine sheets and the number of the fractional medicines; and determining whether a medicine name and a number of medicines in acquired prescription information and the detected medicine name of the one or more medicine sheets and the detected total number of medicines match each other.

12. The dispensing inspection method according to claim 11, further comprising: irradiating the one or more medicine sheets from a lateral side of the first mounting table in capturing the second image.

13. The dispensing inspection method according to claim 11,
wherein in capturing the third image, an angle formed by the optical axis for capturing the third image and the optical axis of light emitted to the second mounting table is 30° to 60°.

14. The dispensing inspection method according to claim 11,
wherein light emitted to the second mounting table in capturing the third image is light of which a half-width of a light intensity in an orientation distribution is 20° to 60°.

15. The dispensing inspection method according to claim 11, further comprising:
detecting the number of fractional medicines using brightness and darkness of the third image.

16. The dispensing inspection method according to claim 11, further comprising: performing edge detection to detect an end face of a sheet-like material from the second image, and detecting the number of the one or more medicine sheets from the second image using at least one of the shape of an end portion of the detected end face, a density between the detected end faces, a density within the detected end faces, the thickness of the detected end face, and regularity of images between the detected end faces.

17. The dispensing inspection method according to claim 11,
wherein a light source of light emitted to the second mounting table in capturing the third image has an elongated shape, and a length thereof in a longitudinal direction is equal to or longer than a length, in a direction that matches a longitudinal direction of inclined illumination, of an imaging region set on the second mounting table.

18. The dispensing inspection method according to claim 11, wherein the first mounting table is inclined with respect to a horizontal direction.

19. The dispensing inspection method according to claim 11, wherein the first mounting table includes positioning means vertically provided with respect to the first mounting table for determining a position of the one or more medicine sheets on the first mounting table.

20. A non-transitory computer-readable recording medium storing a program causing a computer to execute:
- a step of causing first imaging means to capture a first image obtained by imaging one or more medicine sheets that are placed on a first mounting table and are irradiated with diffused light from a lower side thereof, from the lower side of the first mounting table, and causing second imaging means to capture a second image of the one or more medicine sheets from a lateral side of the first mounting table;
- a step of causing third imaging means to capture a third image obtained by imaging fractional medicines cut from the one or more medicine sheets, placed on the second mounting table, and irradiated with light from a lower side thereof in a state where an optical axis of the light is inclined with respect to an optical axis for imaging, from the lower side of the second mounting table;
- a step of detecting a medicine name of the one or more medicine sheets using at least one of Optical Character Recognition (OCR) and code recognition from the first image;
- a step of detecting the number of the one or more medicine sheets from the second image, detecting the number of fractional medicines from the third image, and detecting a total number of medicines from the number of the one or more medicine sheets and the number of the fractional medicines; and
- a step of determining whether a medicine name and a number of medicines in acquired prescription information and the detected medicine name of the one or more medicine sheets and the detected total number of medicines match each other.

* * * * *